(12) United States Patent
Cattell (10) Patent No.: US 7,027,930 B2
(45) Date of Patent: Apr. 11, 2006

(54) READING CHEMICAL ARRAYS

(75) Inventor: Herbert F. Cattell, Mountain View, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 417 days.

(21) Appl. No.: 09/775,163

(22) Filed: Jan. 31, 2001

(65) Prior Publication Data

US 2002/0102558 A1   Aug. 1, 2002

(51) Int. Cl.
*G06T 7/60* (2006.01)
*G06K 9/34* (2006.01)
*G06K 9/20* (2006.01)

(52) U.S. Cl. .......................... 702/19; 702/22; 382/282; 382/286; 382/305

(58) Field of Classification Search .................. 702/19, 702/22; 382/282, 286, 305; 435/174
See application file for complete search history.

(56) References Cited

U.S. PATENT DOCUMENTS 6,591,196 B1 * 7/2003 Yakhini et al. ............... 702/28
6,633,659 B1 * 10/2003 Zhou .......................... 382/129

OTHER PUBLICATIONS

Yang et al. (University of California, Berkeley Technical Report # 584, Nov. 2000).*
GenePix Pro Array Analysis Software and Scanner (Nov. 2000).*
"Affymetrix Jaguar Software", 2pp., printed from http://www.affymetrix.com/products/jaguar.html on Jan. 30, 2001.

* cited by examiner

*Primary Examiner*—Marjorie A. Moran
*Assistant Examiner*—Lori A. Clow
(74) *Attorney, Agent, or Firm*—Gordon Stewart

(57) ABSTRACT

Methods of using an addressable array of biopolymers which has been exposed to a sample, and apparatus and computer program products for use of the arrays. In one embodiment the method includes detecting signals from the exposed array to obtain a signal image of the array. The array signal image is saved in a memory. Based on the detected signals, a shape of each region in one or more sets of multiple regions on the array signal image is established. A definition of the shapes of the established regions of each set is saved in a memory. Each region of each set is processed according to a corresponding routine for that set.

39 Claims, 4 Drawing Sheets

READING CHEMICAL ARRAYS

FIELD OF THE INVENTION

This invention relates to arrays, particularly biopolymer arrays (such polynucleotide arrays, and particularly DNA arrays) which are useful in diagnostic, screening, gene expression analysis, and other applications.

BACKGROUND OF THE INVENTION

Arrays of biopolymers, such as arrays of peptides or polynucleotides (such as DNA or RNA), are known and are used, for example, as diagnostic or screening tools. Such arrays include regions (sometimes referenced as features or spots) of usually different sequence biopolymers arranged in a predetermined configuration on a substrate. The arrays, when exposed to a sample, will exhibit a pattern of binding which is indicative of the presence and/or concentration of one or more components of the sample, such as an antigen in the case of a peptide array or a polynucleotide of particular sequence in the case of a polynucleotide array. The binding pattern can be detected by reading the array, for example, by observing a fluorescence pattern on the array following exposure to a fluid sample in which all potential targets (for example, DNA) in the sample have been labeled with a suitable fluorescent label.

Methods of fabricating biopolymer arrays can be fabricated using light directed methods, in situ synthesis methods or deposition of the previously obtained biopolymers. In known light directed synthesis methods the aim is to form an array of oligonucleotides on a surface by removing a photoremovable group from a surface, coupling a monomer to the exposed region of the surface, and repeating the process. The in situ synthesis methods include those described in U.S. Pat. No. 5,449,754 for synthesizing peptide arrays, as well as WO 98/41531 and the references cited therein for synthesizing polynucleotides (specifically, DNA). Such in situ synthesis methods can be basically regarded as iterating the sequence of depositing droplets of: (a) a protected monomer onto predetermined locations on a substrate to link with either a suitably activated substrate surface (or with a previously deposited deprotected monomer); (b) deprotecting the deposited monomer so that it can now react with a subsequently deposited protected monomer; and (c) depositing another protected monomer for linking. Different monomers may be deposited at different regions on the substrate during any one iteration so that the different regions of the completed array will have different desired biopolymer sequences. One or more intermediate further steps may be required in each iteration, such as oxidation and washing steps.

The "deposition method" basically involves depositing previously obtained biopolymers at predetermined locations on a substrate which are suitably activated such that the biopolymers can link thereto. The deposited biopolymers may, for example, be obtained from synthetic or biological sources. Biopolymers of different sequence may be deposited at different regions of the substrate to yield the completed array. Washing or other additional steps may also be used. Typical procedures known in the art for deposition of polynucleotides, particularly DNA such as whole oligomers or cDNA, are to load a small volume of DNA in solution in one or more drop dispensers such as the tip of a pin or in an open capillary and, touch the pin or capillary to the surface of the substrate. Such a procedure is described in U.S. Pat. No. 5,807,522. When the fluid touches the surface, some of the fluid is transferred. The pin or capillary must be washed prior to picking up the next type of DNA for spotting onto the array. This process is repeated for many different sequences and, eventually, the desired array is formed. Alternatively, the DNA can be loaded into a drop dispenser in the form of an inkjet head and fired onto the substrate. Such a technique has been described, for example, in PCT publications WO 95/25116 and WO 98/41531, and elsewhere. This method has the advantage of non-contact deposition. Still other methods include pipetting and positive displacement pumps such as the Biodot equipment (available from Bio-Dot Inc., Irvine Calif., USA).

In array fabrication, the quantities of DNA available for the array are usually very small and expensive. Sample quantities available for testing are usually also very small and it is therefore desirable to simultaneously test the same sample against a large number of different probes on an array. These conditions require use of arrays with large numbers of very small, closely spaced spots (features). For example, typical arrays may contain more than a thousand or ten thousand features in an area no larger than about 2 to 4 $cm^2$. During array fabrication however, the resulting fabricated array may not have an actual layout which is precisely the same as a target layout. For example, some features actually deposited may have errors in position, dimensions, or presence (and may not be present at all due to intermittent errors in the drop deposition apparatus).

Thus, during reading of an array by a user following exposure to a sample, a determination should be made as to the exact shape of regions that represent actual features. Incorrectly designating regions as features or otherwise incorrectly calculating a total signal value for a feature in a determination of results from the exposed array, can read to serious errors in result interpretation. Determination of array features can be done manually by an operator viewing a display of a signal image acquired from a sample exposed array, and manually designating (with a mouse or other graphical computer pointer device) features based on a subjective evaluation of the boundaries of strong signal regions. The results for such manually designated feature regions can then be processed by known routines (such as by adding the signal values of each pixel within designated features of a digital signal image to obtain a total feature signal value). However, with thousands of features on each array, such a manual procedure is very slow, and does not lend itself to reproducible results. Therefore, computer implemented routines which automatically determine feature (or other region) boundaries are preferred particularly where many sample exposed arrays are to be read and analyzed in an efficient high-throughput manner. These routines and subsequent processing of features to obtain processed results for each (such as final signal values for each feature), are referred to as feature extraction.

However, the present invention recognizes that even sophisticated feature extraction routines will not be able to account for every possible error in designating feature shapes. For example, a routine which establishes a feature boundary based only on regions of highest signal strength, may fail to recognize a region where features have been smeared due to a scratch or other contact with the array. The present invention recognizes then that while automated feature extraction methods are needed for high-throughput reading and processing of array data, it would be desirable to have some convenient and rapid method by which an operator or some other means can review what shapes (for example, feature boundaries) were assigned. The present invention further recognizes that while this can be reproduced by running the same feature extraction program on the raw signal data acquired during array reading such a method is computationally intensive and therefore time consuming. Thus, the present invention realizes that it would be desirable, particularly where many arrays are subject to automated feature extraction, to have some method by which an individual or other means can readily review the shapes assigned to feature or other regions even after feature extraction.

SUMMARY OF THE INVENTION

The present invention then, provides in one aspect, a method of using an addressable array of biopolymers (for example, peptides, or polynucleotides such as DNA or RNA) on a substrate which array has been exposed to a sample. The method includes detecting signals from the exposed array to obtain a signal image of the array and optionally saving the array signal image in a memory. Based on the detected signals, a shape of each region in one or more sets of multiple regions on the array signal image, is established. Such sets may include, for example, regions which represent detected array features or local background regions (discussed further below). The shapes of the established regions of each set is saved in a memory, and each region of each set processed according to a corresponding routine for that set. The displayed shapes may optionally be saved in a first file and at least some, or the majority, of the processed results may be saved in a second file. These files may, for example, both be saved in a non-volatile memory. It will be appreciated that where the detected signals have been previously detected and saved a method of the present invention need not necessarily include the detecting and saving of the signal image.

In another aspect, the method may include retrieving the saved shapes of the established regions from the memory and displaying images of them. This retrieval may particularly be performed prior to retrieving from the memory the majority (that is, greater than 50%, and optionally greater than 60% or 80%) or any of other processed data for each region of each set of the retrieved shapes, which data was processed according to a corresponding routine for that set. Optionally, the array signal image may also be retrieved and the retrieved region shapes and array signal images displayed as overlaid images. In one embodiment, each displayed region may be linked to processed data for that region. This may be accomplished using a graphical user interface in which an individual viewing the displayed region may retrieve saved data (such as the processed results for the corresponding region) simply by selecting any desired region of interest (for example, by pointing and clicking on any region of interest). The method may further optionally include altering a result obtained from the processing of a region based on the displayed shapes of the established regions, for example in response to an alteration of the shape of the displayed region by a user. The present invention further provides a method in which a sub-set of a set of processed data from an addressable array of biopolymers which was exposed to a sample, is retrieved from a memory (such as a non-volatile memory). Optionally, the retrieved data may be reviewed and additional processed data of the set retrieved from the non-volatile memory based on the results of the review. The sub-set retrieved may, for example, be from regions of any one or more sets of regions as discussed herein. For example, an operator (or a suitably programmed processor) may review an initially retrieved sub-set (such as shapes of regions of one or more sets) on a display and, if such data appears questionable (that is, some part or all of it appears to be outside predetermined limits), may then retrieve further data to confirm or dismiss an error (such as in the data or the exposed array). Such a method can, for example, be operated to facilitate rapid review of processed data from multiple different arrays, by allowing the operator to initially review for each only a predetermined sub-set expected to most likely reveal an error. If no error is detected during a sub-set review for an array, review of further processed data for the same array may be avoided thereby saving time during a review of the data for the multiple arrays while still retaining a relatively high level of confidence that an error for that array is unlikely.

Different sets of regions may be established according to any desired feature extraction routine. For example, the shape of regions of a first set are established which comprise regions of signal strength higher than a predetermined value and which represent detected array features surrounded by regions of lower signal strength representing detected background. Similarly, the shape of regions of a second set may be established each of which comprises a local background region of lower signal strength than a corresponding detected feature about which the background region is positioned.

Various region processing routines may be used as desired by a feature extraction procedure. For example, a first routine for processing a set of regions (such as detected features) may include summing signal strength within sub-regions of each first set region to provide a total signal strength for each first set region. The sub-regions may, for example, be pixels or pixel blocks or groups where the signal image is a digital image. Other options include subtracting local background region signal strength from the corresponding detected feature signal strength (for example, by subtracting average local background pixel values from each pixel of the corresponding detected feature).

The present invention further provides an apparatus for using an addressable array of biopolymers on a substrate which array has been exposed to a sample. The apparatus may include a processor, and optionally may also include a detector to detect signals from the exposed array to obtain a signal image of the array and also optionally a memory. The processor is capable of executing any steps of a method of the present invention (other than detecting the actual signals from the array, which is performed by the detector). For example, the processor may save the array signal image in the memory and establish, based on the detected signals, a shape of each region in one or more sets of multiple regions on the array signal image. The processor may further save the definition of the shapes of the established regions of each set in a memory, and process each region of each set according to a corresponding routine for that set. It will be appreciated that the detected signals from the array may have been previously detected and saved and thus, an apparatus of the present invention need not necessarily include a detector and the processor need not necessarily perform the signal image saving.

The present invention further provides a computer program product, comprising: a computer readable storage medium having a computer program stored thereon. The computer program may perform any one or more of the steps required by a method of the present invention (other than the array signal detection), in any different combinations. In another aspect, the computer program performs, when loaded into a computer, the steps of: receiving signals from a biopolymer array which has been exposed to a sample, as a signal image of the array; saving the array signal image in a memory; establishing, based on the detected signals, a shape of each region in one or more sets of multiple regions on the array signal image; saving a definition of the shapes of the established regions of each set in a memory; and processing each region of each set according to a corresponding routine for that set. The saving of the signal image into memory may be omitted where this has been previously done and the memory made accessible to the program. In another aspect, the computer program may perform the steps of retrieving the signal image and shape definitions and displaying them as overlaid images, without necessarily performing other steps.

One or more of the various aspects of the present invention may provide one or more of the following, or other, useful benefits. For example, region shape definitions for one or more arrays can be quickly reviewed to facilitate detection of a potential problem in the application of an automatic feature extraction routine to a particular array in a large batch of automatically extracted arrays.

BRIEF DESCRIPTION OF THE DRAWINGS

Embodiments of the invention will now be described with reference to the drawings in which.

To facilitate understanding, identical reference numerals have been used, where practical, to designate identical elements that are common to the figures.

DETAILED DESCRIPTION OF THE INVENTION

In the present application, unless a contrary intention appears, the following terms refer to the indicated characteristics. A "biopolymer" is a polymer of one or more types of repeating units. Biopolymers are typically found in biological systems and particularly include polysaccharides (such as carbohydrates), and peptides (including polypeptides and proteins) and polynucleotides as well as such compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides.

An "array", unless a contrary intention appears, includes any one, two or three dimensional arrangement of addressable regions bearing a particular chemical moiety or moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers collectively to one or more characteristics of the features, such as feature positioning, one or more feature dimensions, errors, or some indication of a moiety at a given location. "Hybridizing" and "binding", with respect to polynucleotides, are used interchangeably.

When one item is indicated as being "remote" from another, this is referenced that the two items are at least in different buildings, and may be at least one mile, ten miles, or at least one hundred miles apart. "Communicating" information references transmitting the data representing that information as electric or electromagnetic (including light) signals over a suitable communication circuit or channel. It will also be appreciated that throughout the present application, that words such as "top", "upper", and "lower" are used in a relative sense only. "Fluid" is used herein to reference a liquid. A "set" or a "sub-set" may have one or more members but a set of multiple members has more than one. A "processor" includes any one or more electrical and/or optical processors which can execute all the steps required of it, or any hardware or software combination which will perform those or equivalent steps, such as one or more general purpose digital microprocessors suitably programmed from a computer readable medium carrying necessary program code. Any "memory" includes any suitable device or combination of devices in which a processor can store and/or retrieve data as required, and includes: non-volatile memory which remains without a source of power, such as magnetic, optical, or certain solid state storage devices (for example, magnetic or optical disks or tape or non-volatile memory chips) as well as volatile memory (for example, volatile memory chips). Any memory may be either fixed or portable. Steps recited in a particular order in relation to any method can be carried out in the recited order or changed in order where this is logically possible and not otherwise indicated. Reference to a singular item, includes the possibility that there are plural of the same items present. All patents, patent applications, and other cited references are incorporated into this application by reference except to the extent that anything in them conflicts with the present application.

Figures 1, 2:
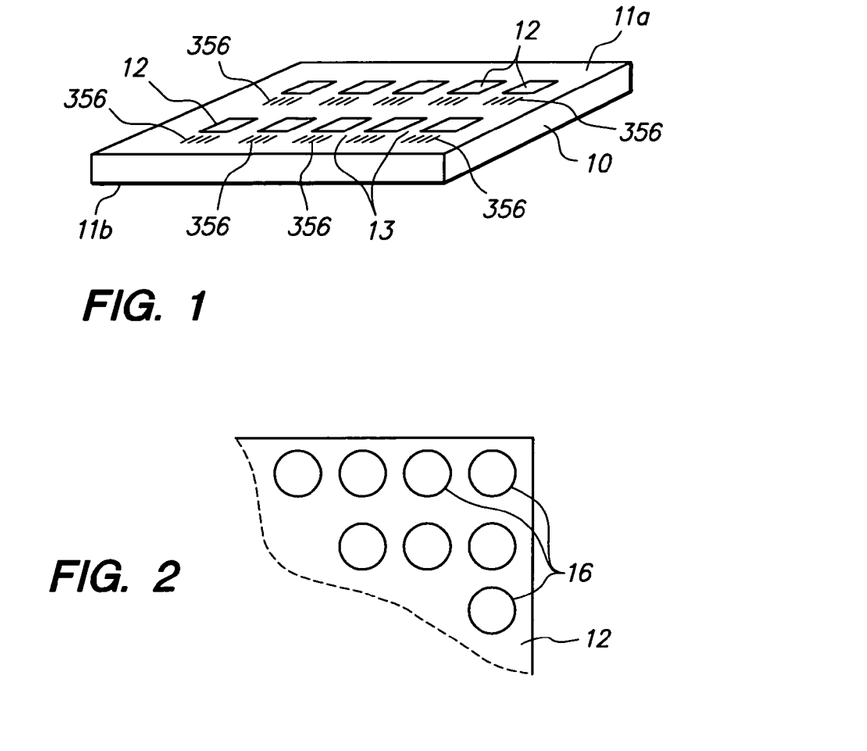
FIG. 1 illustrates a substrate carrying multiple arrays, such as may be used in methods and apparatus of the present invention.
FIG. 2 is an enlarged view of a portion of FIG. 1 showing multiple ideal spots or features.
Figure 3:
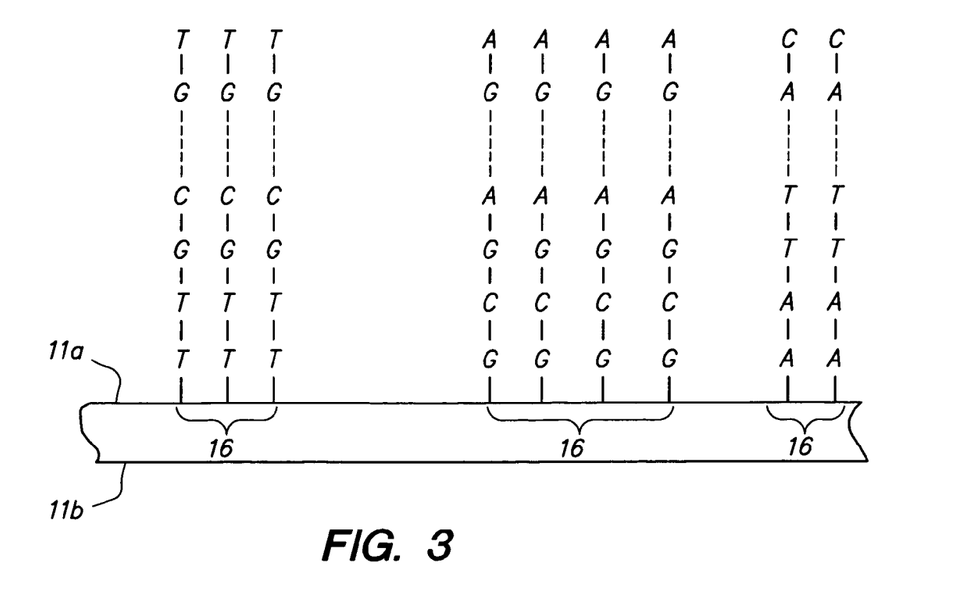
FIG. 3 is an enlarged illustration of a portion of the substrate in FIG. 2.

Referring first to FIGS. 1–3, methods and apparatus of the present invention may be used with a contiguous planar substrate 10 carrying one or more arrays 12 disposed across a front surface 11a of substrate 10 and separated by inter-array areas 13. A back surface 11b of substrate 10 does not carry any arrays 12. The arrays on substrate 10 can be designed for testing against any type of sample, whether a trial sample, reference sample, a combination of them, or a known mixture of polynucleotides (in which latter case the arrays may be composed of features carrying unknown sequences to be evaluated). While ten arrays 12 are shown in FIG. 1 and the different embodiments described below may use a substrate with only one array 12 on it, it will be understood that substrate 10 and the embodiments to be used with it may have any number of desired arrays 12. Similarly, substrate 10 may be of any shape, and any apparatus used with it adapted accordingly. Depending upon intended use, any or all of arrays 12 may be the same or different from one another and each will contain multiple spots or features 16 of biopolymers such as polynucleotides. A typical array may contain from more than ten, more than one hundred, more than one thousand or ten thousand features, or even more than from one hundred thousand features. All of the features 16 may be different, or some or all could be the same. In the embodiment illustrated, there are interfeature areas 17 between features, which do not carry any polynucleotide. It will be appreciated though, that the interfeature areas 17 could be of various sizes and configurations. It will be appreciated that there need not be any space separating arrays 12 from one another, nor features 16 within an array from one another. However, in the case where arrays 12 are formed by the deposition method as described above, such inter-array and inter-feature areas 17 will typically be present. Each feature carries a predetermined polynucleotide (which includes the possibility of mixtures of polynucleotides). As per usual, A, C, G, T represent the usual nucleotides. It will be understood that there may be a linker molecule (not shown) of any known types between the front surface 11a and the first nucleotide.

FIGS. 2 and 3 are enlarged views illustrating portions of ideal features on an array where the actual features formed are the same as the desired features (sometimes referenced as the "target" or "aim" features), with each feature 16 being uniform in shape, size and composition, and the features being regularly spaced. In practice though, such an ideal result is not obtained with there being some error in one or more feature characteristics.

Arrays such as arrays 12 may be fabricated at a fabrication station using in situ or deposition techniques, as more fully described, for example, in U.S. patent application Ser. No. 09/302898 for "Polynucleotide Array Fabrication" filed Apr. 30, 1999 by Caren et al.

Figure 4:
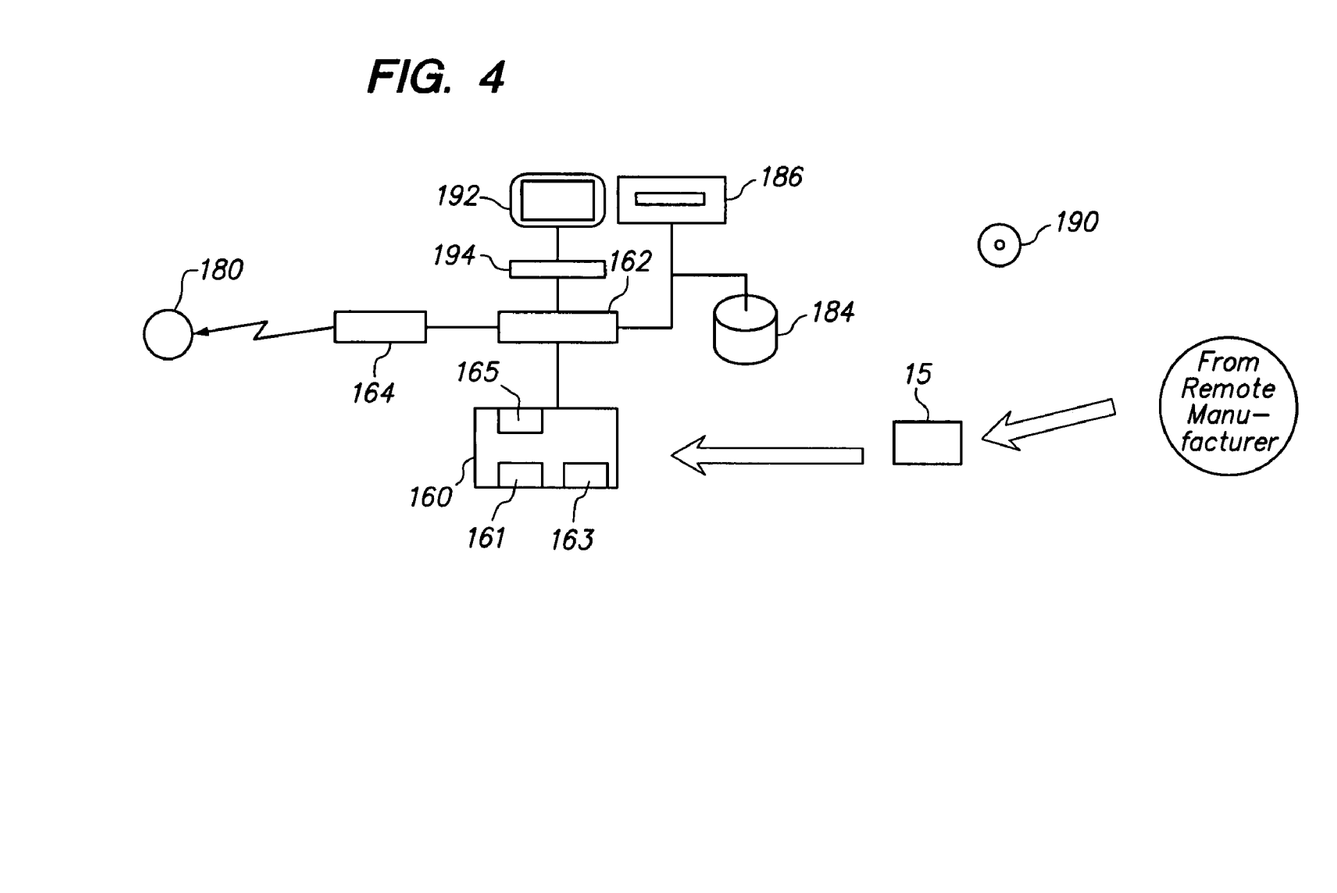
FIG. 4 is a schematic diagram of an apparatus at a user site which can execute a method of the present invention.

FIG. 4 illustrates an apparatus of the present invention at which an addressable array 12 may be used, in particular a single "user station" which may or may not be remote from the fabrication station (usually at the location of the customer which ordered a received array 12). The user station includes a processor 162, a non-volatile memory 184, user input device 194 (such as a keyboard and/or mouse or touch screen), monitor 192, an array reader in the form of a scanner 160 to read an array following exposure to a sample, data writer/reader 186 (which may be capable of writing/reading to the same type of media as writer/reader 320), and a communication module 164 which also has access to a communication channel 180. Processor 162 can be programmed from any computer readable medium carrying a suitable computer program which may be read locally (such as by reader/writer 186) or from a remote location through communication channel 180. Scanner 160 may include a holder 161 which receives and holds an array unit 15, as well as a source of illumination (such as a laser) and a detector in the form of light sensor 165 to read fluorescent light signals from respective features on the array. Communication module 164 may be any type of suitable communication module, such as telephone modem, WAN card, or satellite modem card. Scanner 160 can be any suitable apparatus for reading an array, such as one which can read the location and intensity of fluorescence at each feature of an array following exposure to a fluorescently labeled sample. For example, such a scanner may be similar to the GENEARRAY scanner available from Hewlett-Packard, Palo Alto, Calif. The scanning components of scanner 160, holder 161, and reader 163 may all be contained within the same housing of a single same apparatus.

Figure 5:
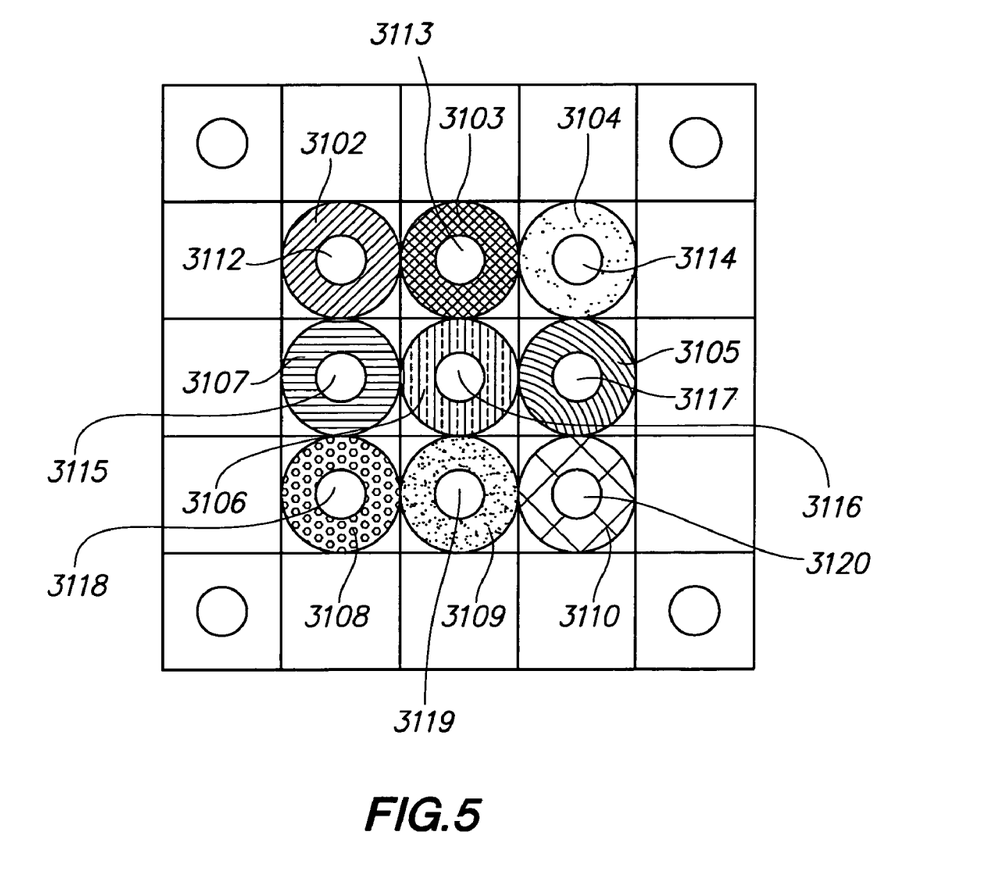
FIG. 5 illustrates the display of image and region shapes for a read array.
Figure 6:
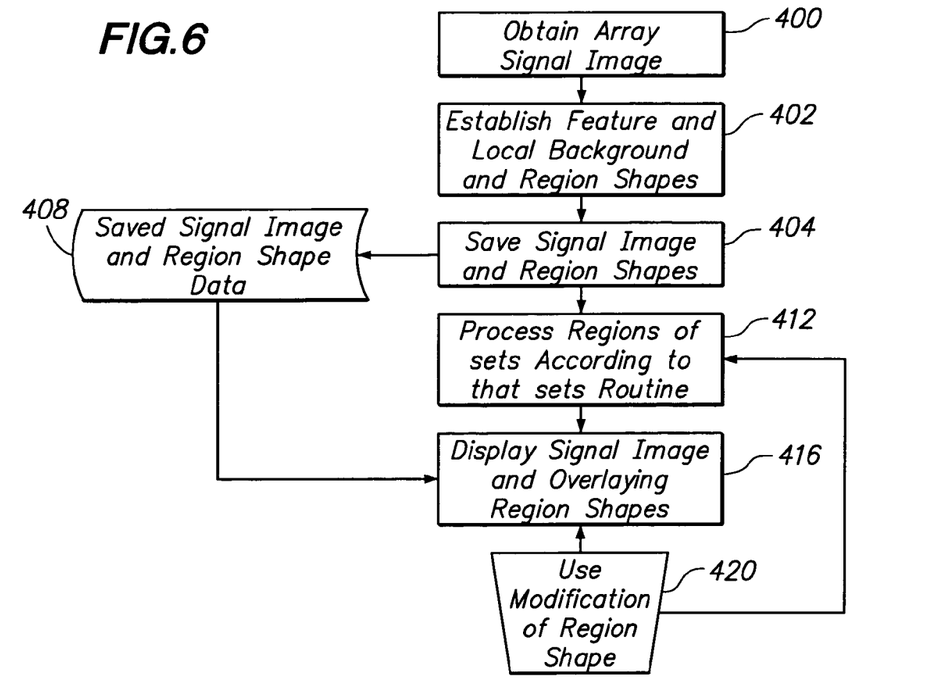
FIG. 6 is a flowchart illustrating a method of the present invention.

The operation of the user station of FIG. 4 will now be described with reference to FIGS. 4–6. Steps and data in FIG. 6 are referenced by numerals in parentheses. In FIG. 4, an array in the form of an array unit 15 is received from the remote fabrication station. Unit 15 includes one or more arrays 12 on substrate 10 and optionally in a housing (which may include a closed chamber accessible through one or more ports normally closed by septa). A sample, for example a test sample, is exposed to the array 12 on the array unit 15. Following hybridization and washing in a known manner, the array unit 15 is then inserted into holder 161 in scanner 160 for reading of the array (such as information representing the fluorescence pattern on the array 12) under control of processor 162. During reading signals from light sensor 165 are obtained (400) at processor 162 in the form of a digital signal image. The digital signal image is merely a spatial representation of the detected pixels each associated with its corresponding signal value. The signal value may, for example, simply be a level on a digital scale (for example, an 8 or 10 bit scale for any single color) and may be displayed on a monitor 192 as varying brightness. Detector 165 may, for example, provide an image signal with a pixel resolution of about 2 to 4 μm where each feature has an approximate diameter of about 10 to 30 μm. Shapes for detected features and local background regions around respective features, are established (402) by processor 162 based on a predetermined algorithm. For example, pixels in a group which have a signal strength higher than a predetermined value, may be established as the shape of a detected feature. Pixels around and within a certain number of pixels of an outer boundary of a detected feature, and which have signal strength lower than any pixels of a corresponding detected feature may be established as a local background region for that feature. In this manner, detected features (which form a first set of multiple regions) with their surrounding local backgrounds (forming a second set of multiple regions) may be established. Other sets of multiple regions may include inlier or outlier regions within an array feature or background feature. The definition of the shapes of these sets of regions, when displayed, results in an image such as that of FIG. 5 in which local backgrounds 3102–3110 surround respective detected features 3112–3120. The digital signal image and the definition of the shapes are saved (404) in memory 184 as data signal image and region shape data (408). For example, the shape definitions and optionally the digital signal image may be saved in any known image format such as JPEG, TIFF, uncompressed bitmapped, vector mapped, or the like. The regions of each set may then be processed according to the routine for that set. For example, pixels (which are sub-regions) of a detected feature may have their digital signal strength values summed to provide a total signal strength for each feature. Prior to such summation a background value such as an average of a local background pixel value for a feature, may be subtracted from each pixel of the feature surrounded by that local background region. Aspects and different routines used during feature extraction are further discussed in U.S. patent application Ser. No. 09/659415 filed Sept. 11, 2000 for "Method And System For Extracting Data From Surface Array Deposited Features". Note that the shapes of the sets of regions may be saved in memory 184 in a first file, while the processed results are saved in a second file (each file having its own identifier or name). This permits fast retrieval and display of the shapes before the retrieval of the processed results. Some of the processed results can also be saved in the first file (such as less than 5%, 10% 20%, 40%, or less than 50% of the total bits of the processed results). However, regardless of the format of the saved shapes and processed information, the saved shapes may be retrieved and displayed by processor 162 from memory 184 prior to retrieving the majority of other processed data for the retrieved and displayed shapes.

Many arrays can be read and processed rapidly and automatically by scanner 160 under control of processor 162. At any suitable time subsequent to processing each established region of an array (such as the detected features and local backgrounds) the saved signal image and region shape data (408) can be retrieved and displayed (416) as overlaid images. These have the appearance of FIG. 5 but additionally including the image signal pixels with signal strength displayed as increased brightness. Note that the established shapes can be displayed as solid shapes or as boundaries, such as just the outer boundaries of the detected features and local background regions. A user may evaluate the results from the processing based on the display of the shapes at any time (for example, a detected feature shape which deviates more than a predetermined amount from an expected circular shape may indicate a processed result from that feature to be unreliable). The retrieval and display can be done either continuously during scanning and reading for each array of a batch of arrays, or at any time subsequently. Processor 162 may link regions such as detected features with processed data from that region, such that a user can access that data with an appropriate command to select the corresponding region. For example, with an appropriate graphical user interface a user can point and click on a displayed detected feature using user input device 194 and the processed data (for example, total signal strength for that feature) is retrieved and displayed in a window on monitor 192. This facilitates a user evaluating whether the established shape may be in error. Additionally, the graphical user interface allows the user to use input device 194 to alter a parameter used in the processing such as by altering the shape of region on display 192. This can be done, for example, by dragging a boundary of a detected feature or local background region. Processor 162 then re-processes the altered region according to the same routine previously used (such as the pixel signal addition routine described above in connection with detected features) using the altered shape.

Results from the array reading can include the processed results discussed above. The results of the reading (processed or not) can be forwarded (such as by communication) along with data (408) to be received at a remote location for further evaluation and/or processing, or use, using communication channel 180 or reader/writer 186 and medium 190. This data may be transmitted by others as required to reach the remote location, or re-transmitted to elsewhere as desired.

Modifications in the particular embodiments described above are, of course, possible. For example, where a pattern of arrays is desired, any of a variety of geometries may be constructed other than the organized rows and columns of arrays 12 of FIG. 1. For example, arrays 12 can be arranged in a series of curvilinear rows across the substrate surface (for example, a series of concentric circles or semi-circles of spots), and the like. Similarly, the pattern of regions 16 may be varied from the organized rows and columns of spots in FIG. 2 to include, for example, a series of curvilinear rows across the substrate surface (for example, a series of concentric circles or semi-circles of spots), and the like. Even irregular arrangements of the arrays or the regions within them can be used provided the locations of features of identified biopolymers are known.

The present methods and apparatus may be used to deposit biopolymers or other moieties on surfaces of any of a variety of different substrates, including both flexible and rigid substrates. Thus, in any of the above described methods "biopolymer" or "biopolymers" could more broadly be replaced with "moiety" or "moieties". Preferred materials for the substrate provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used, particularly when such are cut after fabrication into smaller size substrates carrying a smaller total number of arrays 12. Substrates of other configurations and equivalent areas can be chosen. The configuration of the array may be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like).

The substrate surface onto which the polynucleotide compositions or other moieties is deposited may be porous or non-porous, smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated), Various further modifications to the particular embodiments described above are, of course, possible. Accordingly, the present invention is not limited to the particular embodiments described in detail above.

What is claimed is:

1. A method of reading an addressable array of biopolymers on a substrate which array has been exposed to a sample, comprising:
   (a) detecting signals from the exposed array to obtain a signal image of the array;
   (b) establishing, based on the detected signals, a shape of each region in one or more sets of multiple regions on the array signal image, and displaying the established shapes, wherein the shape of regions of a set include an identified shape of any of an array feature, a background region, and an identified inlier or outlier region within an array feature or background region;
   (c) processing each region of each set according to a region processing routine; and
   (d) saving the displayed shapes in a first file and the processed results in a second file.

2. The method according to claim 1 wherein the biopolymers are polynucleotides.

3. The method according to claim 2 wherein the biopolymers are DNA.

4. The method according to claim 1 wherein the first file is smaller than the second file.

5. The method according to claim 4 wherein the shape of regions of a second set are established each of which comprises a local background region of lower signal strength than a corresponding detected feature about which the background region is positioned.

6. The method according to claim 5 wherein the first routine comprises subtracting local background region signal strength from the corresponding detected feature signal strength.

7. The method according to claim 1 additionally comprising, subsequent to processing of each region, retrieving the saved shapes of the established regions and displaying images of them.

8. The method according to claim 7 wherein the shape of regions of a first set are established which comprise regions of signal strength higher than a predetermined value representing detected array features, surrounded by regions of lower signal strength representing detected background.

9. The method according to claim 8 wherein the regions of the first set are processed by a first routine comprising a summation of signal strength within sub-regions of each first set region to provide a total signal strength for each first set region.

10. The method according to claim 9 wherein the array signal image is a digital signal image and the sub-regions are pixels or pixel blocks.

11. The method according to claim 1 additionally comprising, saving the array signal image, and subsequent to processing each region, retrieving the array signal image and saved shapes of the established regions and displaying overlaid images of them.

12. The method according to claim 11 wherein each displayed region is linked to processed results for that region.

13. The method according to claim 12 additionally comprising evaluating the results from the processing based on the displayed retrieved shapes.

14. The method according to claim 12 additionally comprising, based on the displayed retrieved shapes, altering a parameter used in the processing and re-processing a region using the altered parameter.

15. The method according to claim 11 additionally comprising re-processing a region in response to an alteration of one of the shapes of a set using the altered shape.

16. A computer program product, comprising: a computer readable storage medium having a computer program stored thereon for performing, when loaded into a computer, the steps of:
   (a) receiving signals from a biopolymer array which has been exposed to a sample, as a signal image of the array;
   (b) saving the array signal image in a memory;
   (c) establishing, based on the detected signals, a shape of each region in one or more sets of multiple regions on the array signal image, wherein the shape of regions of a set include an identified shape of any of an array feature, a background region, and an identified inlier or outlier region within an array feature or background region;
   (d) saving a definition of the shapes of the established regions of each set in a memory; and
   (e) processing each region of each set according to a region processing routine.

17. A method of reading an addressable array of biopolymers on a substrate which array has been exposed to a sample, comprising:
   (a) detecting signals from the exposed array to obtain a signal image of the array;
   (b) establishing, based on the detected signals, a shape of each region in one or more sets of multiple regions on the array signal image, and displaying the established shapes, wherein the shape of regions of a set include an identified shape of an inlier or outlier region within an array feature;
   (c) processing each region of each set according to a region processing routine; and
   (d) saving the displayed shapes in a first file and the processed results in a second file.

18. The method according to claim 17 wherein the biopolymers are polynucleotides.

19. The method according to claim 18 wherein the biopolymers are DNA.

20. The method according to claim 17 wherein the first file is smaller than the second file.

21. The method according to claim 17 additionally comprising, subsequent to processing of each region, retrieving the saved shapes of the established regions and displaying images of them.

22. The method according to claim 17 additionally comprising, saving the array signal image, and subsequent to processing each region, retrieving the array signal image and saved shapes of the established regions and displaying overlaid images of them.

23. The method according to claim 22 wherein each displayed region is linked to processed results for that region.

24. The method according to claim 23 additionally comprising evaluating the results from the processing based on the displayed retrieved shapes.

25. The method according to claim 23 additionally comprising, based on the displayed retrieved shapes, altering a parameter used in the processing and re-processing a region using the altered parameter.

26. The method according to claim 22 additionally comprising re-processing a region in response to an alteration of one of the shapes of a set using the altered shape.

27. A computer program product, comprising: a computer readable storage medium having a computer program stored thereon for performing, when loaded into a computer, the steps of:
  (a) receiving signals from a biopolymer array which has been exposed to a sample, as a signal image of the array;
  (b) saving the array signal image in a memory;
  (c) establishing, based on the detected signals, a shape of each region in one or more sets of multiple regions on the array signal image, wherein the shape of regions of a set include an identified shape of an identified inlier or outlier region within an army feature;
  (d) saving a definition of the shapes of the established regions of each set in a memory; and
  e) processing each region of each set according to a region processing routine.

28. An apparatus for reading an addressable array of biopolymers on a substrate which array has been exposed to a sample, comprising:
  (a) a detector to detect signals from the exposed array to obtain a signal image of the array;
  (b) a memory; and
  (c) a processor which:
    establishes, based on the detected signals, a shape of each region in one or more sets of multiple regions on the array signal image, wherein the shape of regions of a set include an identified shape of any of an array feature, a background region, and an identified inlier or outlier region within an array feature or background region;
    saves a definition of the shapes of the established regions of each set in a memory;
    processes each region of each set according to a region processing routine; and
    saves the displayed shapes in a first file and the processed results in a second file.

29. The apparatus according to claim 28 wherein the biopolymers are polynucleotides.

30. The apparatus according to claim 29 wherein the regions of the first set are processed by a first routine comprising a summation of signal strength within subregions of each first set region to provide a total signal strength for each first set region.

31. The apparatus according to claim 28 wherein the processor, subsequent to processing of each region, retrieves the saved shapes of the established regions and displays images of them.

32. The apparatus according to claim 28 wherein the processor saves the array signal image in memory and, subsequent to processing each region, retrieves the array signal image and saved shapes of the established regions, and displays overlaid images of them.

33. The apparatus according to claim 32 wherein each displayed region is linked to processed results for that region.

34. The apparatus according to claim 32 wherein the processor, in response to a user input alteration of one of the shapes of a set, reprocesses that region with the altered shape according to the corresponding routine for that set.

35. The apparatus according to claim 28 wherein the shape of regions of a first set are established which comprise regions of signal strength higher than a predetermined value representing detected array features, surrounded by regions of lower signal strength representing detected background.

36. The apparatus according to claim 35 wherein the processor establishes a shape of regions of a second set each of which comprises a local background region of lower signal strength than a corresponding detected feature about which the background region is positioned.

37. The apparatus method according to claim 36 wherein the first routine comprises subtracting local background region signal strength from the corresponding detected feature signal strength.

38. An apparatus for reading an addressable array of biopolymers on a substrate which array has been exposed to a sample, comprising:
  (a) a detector to detect signals from the exposed array to obtain a signal image of the array;
  (b) a memory; and
  (c) a processor which:
    establishes, based on the detected signals, a shape of each region in one or more sets of multiple regions on the array signal image, wherein the shape of regions of a set include an identified shape of an identified inlier or outlier region within an array feature;
    saves a definition of the shapes of the established regions of each Set in a memory;
    processes each region of each set according to a region processing routine; and
    saves the displayed shapes in a first file and the processed results in a second file.

39. The apparatus according to claim 38 wherein the biopolymers are polynucleotides.

* * * * *

UNITED STATES PATENT AND TRADEMARK OFFICE
CERTIFICATE OF CORRECTION

PATENT NO.         : 7,027,930 B2
APPLICATION NO. : 09/775163
DATED              : April 11, 2006
INVENTOR(S)        : Cattell It is certified that error appears in the above-identified patent and that said Letters Patent is hereby corrected as shown below:

In column 13, line 35, in Claim 27, delete "army" and insert -- array --, therefor.

In column 13, line 38, in Claim 27, delete "e)" and insert -- (e) --, therefor.

In column 14, line 21, in Claim 34, delete "reprocesses" and insert -- re-processes --, therefor.

In column 14, line 52, in Claim 38, delete "Set" and insert -- set --, therefor.

Signed and Sealed this

Twenty-eighth Day of November, 2006

JON W. DUDAS
*Director of the United States Patent and Trademark Office*